(12) United States Patent
Suh et al.

(10) Patent No.: US 10,994,265 B2
(45) Date of Patent: May 4, 2021

(54) CATALYST SYSTEM FOR OXIDATIVE DEHYDROGENATION, REACTOR FOR PREPARING BUTADIENE INCLUDING CATALYST SYSTEM, AND METHOD OF PREPARING 1,3-BUTADIENE

(71) Applicant: LG CHEM, LTD., Seoul (KR)

(72) Inventors: Myungji Suh, Daejeon (KR); Dong Hyun Ko, Daejeon (KR); Kyong Yong Cha, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/477,866

(22) PCT Filed: Nov. 27, 2018

(86) PCT No.: PCT/KR2018/014736
§ 371 (c)(1),
(2) Date: Jul. 12, 2019

(87) PCT Pub. No.: WO2019/107884
PCT Pub. Date: Jun. 6, 2019

(65) Prior Publication Data
US 2020/0122126 A1    Apr. 23, 2020

(30) Foreign Application Priority Data

Nov. 30, 2017 (KR) .......................... 10-2017-0162431

(51) Int. Cl.
*B01J 23/80* (2006.01)
*B01J 21/04* (2006.01)
(Continued)

(52) U.S. Cl.
CPC ............... *B01J 23/80* (2013.01); *B01J 21/04* (2013.01); *B01J 35/0026* (2013.01);
(Continued)

(58) Field of Classification Search
CPC ........ B01J 23/80; B01J 21/04; B01J 35/0026; B01J 35/1076; B01J 37/0221
(Continued)

(56) References Cited

U.S. PATENT DOCUMENTS 3,284,536 A    11/1966 Bajars et al.
3,303,234 A *  2/1967 Bajars .................... H02K 11/00
                                               585/618

(Continued)

FOREIGN PATENT DOCUMENTS

AU    2007-274285    8/2010
CN    101328116     12/2008
(Continued)

OTHER PUBLICATIONS

KR 10-2012-0009687_English Translation (Year: 2012).*
(Continued)

*Primary Examiner* — Patricia L. Hailey
(74) *Attorney, Agent, or Firm* — Dentons US LLP

(57) ABSTRACT

Provided is a catalyst system for oxidative dehydrogenation, a reactor for preparing butadiene including the catalyst system, and a method of preparing 1,3-butadiene. In the catalyst system for oxidative dehydrogenation, a coating catalyst is diluted with a specific dilution filler and a reactor is filled with the diluted catalyst, or a reactor is filled with a catalyst for oxidative dehydrogenation so that the concentration of an active ingredient included in the catalyst gradually increases in the direction from reactants inlet in which reactants are fed into the reactor to products outlet. The catalyst system for oxidative dehydrogenation can efficiently control heat generated inside a reactor, thereby improving conversion rate, selectivity, yield, and long-term stability of a catalyst.

13 Claims, 1 Drawing Sheet

(51) Int. Cl.
*B01J 35/00* (2006.01)
*B01J 35/10* (2006.01)
*B01J 37/02* (2006.01)
*C07C 5/48* (2006.01)

(52) U.S. Cl.
CPC ....... *B01J 35/1076* (2013.01); *B01J 37/0221* (2013.01); *C07C 5/48* (2013.01); *C07C 2521/04* (2013.01); *C07C 2523/745* (2013.01); *C07C 2523/80* (2013.01)

(58) Field of Classification Search
USPC ....... 502/102, 318, 324, 340, 343–345, 350, 502/524
See application file for complete search history.

(56) References Cited

U.S. PATENT DOCUMENTS

| | | | |
|---|---|---|---|
| 3,998,760 | A | 12/1976 | Christmann et al. |
| 4,150,064 | A * | 4/1979 | Miklas ..................... B01J 23/80 585/625 |
| 4,469,589 | A * | 9/1984 | Yoo ........................ B01J 21/005 208/113 |
| 6,563,000 | B1 | 5/2003 | Yunoki et al. |
| 2006/0004229 | A1 * | 1/2006 | Dieterle ................ C07C 51/252 562/527 |
| 2010/0121123 | A1 | 5/2010 | Chung et al. |
| 2010/0298601 | A1 | 11/2010 | Choi et al. |
| 2011/0004041 | A1 | 1/2011 | Chung et al. |
| 2012/0130137 | A1 | 5/2012 | Orita et al. |
| 2013/0158325 | A1 | 6/2013 | Kwon et al. |
| 2014/0066680 | A1 * | 3/2014 | Miao ..................... B01J 37/031 585/625 |
| 2014/0163288 | A1 | 6/2014 | Ruttinger et al. |
| 2015/0073184 | A1 * | 3/2015 | Caciula .................... C07C 5/09 585/254 |
| 2016/0023963 | A1 * | 1/2016 | Maat ........................ C07C 2/36 585/329 |
| 2018/0186711 | A1 | 7/2018 | Suh et al. |
| 2018/0214854 | A1 | 8/2018 | Choi et al. |
| 2018/0333702 | A1 | 11/2018 | Suh et al. |
| 2019/0016649 | A1 | 1/2019 | Kim et al. |
| 2019/0201876 | A1 | 7/2019 | Suh et al. |
| 2019/0329226 | A1 * | 10/2019 | Suh ......................... B01J 23/80 |
| 2020/0079710 | A1 * | 3/2020 | Jamaleddine .......... B01J 8/0484 |

FOREIGN PATENT DOCUMENTS

| | | | | |
|---|---|---|---|---|
| CN | 101918126 | | 12/2010 | |
| EP | 3488921 | A2 | 5/2019 | |
| JP | S46-2063 | | 10/1971 | |
| JP | S51-125001 | | 11/1976 | |
| JP | 2008-504309 | | 2/2008 | |
| JP | 2011-006395 | | 1/2011 | |
| JP | 2012-077074 | | 4/2012 | |
| JP | 2013-536066 | | 9/2013 | |
| JP | 2014-198707 | | 10/2014 | |
| JP | 2016-169183 | | 9/2016 | |
| JP | 2018-524159 | | 8/2018 | |
| JP | 2019-528170 | | 10/2019 | |
| KR | 10-0847206 | | 7/2008 | |
| KR | 10-2012-0009687 | * | 2/2012 | ............ B01J 23/889 |
| KR | 10-2012-0026049 | | 3/2012 | |
| KR | 10-2013-0046458 | | 5/2013 | |
| KR | 10-2014-0082869 | | 7/2014 | |
| KR | 10-1508776 | | 3/2015 | |
| KR | 10-2017-0068351 | | 6/2017 | |
| WO | 2012-011659 | | 1/2012 | |
| WO | 2014-138520 | | 9/2014 | |
| WO | 2017046680 | | 3/2017 | |
| WO | 2017-150830 | | 9/2017 | |
| WO | 2018-190642 | | 10/2018 | |
| WO | 2019013473 | | 1/2019 | |

OTHER PUBLICATIONS

Lee, "Preparation, characterization, and catalytic activity of ferrite catalysts for oxidative dehydrogenation of n-butene to 1,3-butadiene," Thesis (Masters), 1st Seoul National University Graduate School (2009) [English Language Abstract included].

* cited by examiner

[FIG. 1]
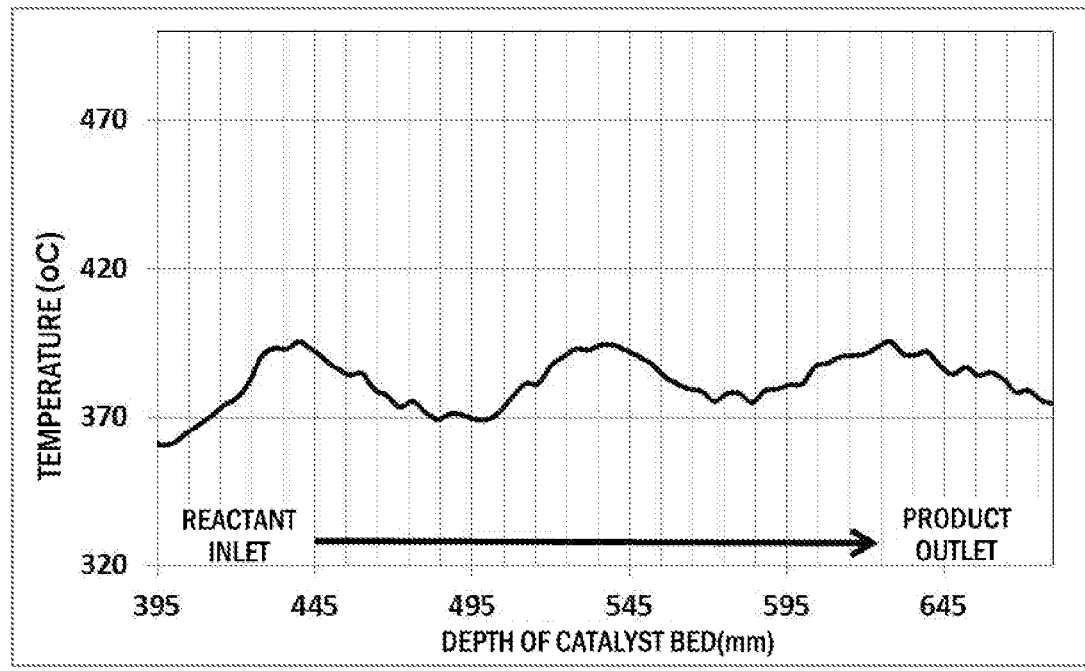
[FIG. 2]
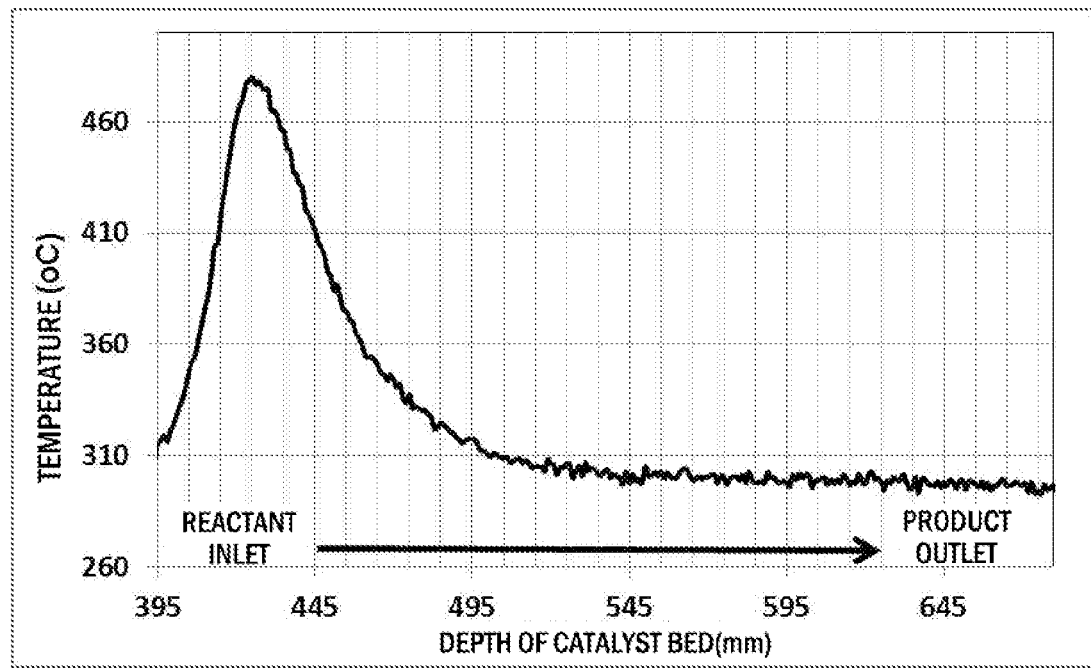

CATALYST SYSTEM FOR OXIDATIVE DEHYDROGENATION, REACTOR FOR PREPARING BUTADIENE INCLUDING CATALYST SYSTEM, AND METHOD OF PREPARING 1,3-BUTADIENE

CROSS-REFERENCE TO RELATED APPLICATIONS

This application is a National Stage Application of International Application No. PCT/KR2018/014736 filed on Nov. 27, 2018, which claims the benefit of Korean Patent Application No. 10-2017-0162431, filed on Nov. 30, 2017, in the Korean Intellectual Property Office, the disclosure of which is incorporated herein in its entirety by reference.

TECHNICAL FIELD

The present invention relates to a catalyst system for oxidative dehydrogenation, a reactor for preparing butadiene including the catalyst system, and a method of preparing 1,3-butadiene. More specifically, the present invention relates to a catalyst system for oxidative dehydrogenation, wherein a coating catalyst having a porous support coated with an active ingredient is diluted with a dilution filler and a reactor is filled with the diluted catalyst, or a reactor is filled with a catalyst for oxidative dehydrogenation so that the concentration of an active ingredient included in the catalyst gradually increases in the direction from reactants inlet in which reactants are fed into the reactor to products outlet. According to the catalyst system of the present invention, heat generated inside a reactor can be efficiently controlled, whereby conversion rate, selectivity, and yield can be greatly improved and long-term stability of a catalyst can be improved.

BACKGROUND ART 1,3-butadiene, a major basic product of petroleum fraction, is a representative raw material used in preparation of synthetic rubber, and the price thereof fluctuates rapidly in connection with supply and demand of the petrochemical industry. Examples of methods of preparing 1,3-butadiene include naphtha cracking, direct dehydrogenation of normal butene, oxidative dehydrogenation of normal butene, and the like.

According to the method of preparing 1,3-butadiene by oxidative dehydrogenation of normal butene, butene and oxygen react in the presence of a metal oxide catalyst to generate 1,3-butadiene and water. In this case, water generated as a result of the reaction is stable. Thus, the method is thermodynamically very advantageous. In addition, since oxidative dehydrogenation of normal butene is an exothermic reaction unlike direct dehydrogenation, reaction can be performed at a low temperature. Thus, 1,3-butadiene can be obtained in high yield while reducing energy consumption. In addition, in the case of oxidative dehydrogenation, since an oxidizing agent is added, the generation amount of carbon deposits which shorten catalyst life by poisoning the catalyst is reduced. Further, since removal of the oxidizing agent is easy, the method of preparing 1,3-butadiene using oxidative dehydrogenation is very suitable for commercialization.

However, heat generated during oxidative dehydrogenation is accumulated in a catalyst bed, deteriorating a catalyst, thereby degrading catalyst life, and side reaction is promoted by excess heat, thereby reducing reaction efficiency. As a result, butadiene yield, selectivity for butadiene, and the conversion rate of butene can be lowered.

To solve these problems, a method of controlling space velocity by controlling the amount of gas fed to a reactor has been proposed. However, this method was unsatisfactory in terms of productivity and yield. Thus, development of a system for oxidative dehydrogenation of butene that can effectively control heat generated inside a reactor while having high productivity is still required.

Prior Art Document

[Patent Document] (Patent Document 1) KR 10-1508776 B1

DISCLOSURE

Technical Problem

Therefore, the present invention has been made in view of the above problems, and it is one object of the present invention to provide a catalyst system for oxidative dehydrogenation capable of effectively controlling heat generated inside a reactor to prevent catalyst deterioration, thereby improving conversion rate, selectivity, and yield.

It is another object of the present invention to provide a reactor for preparing butadiene including the catalyst system for oxidative dehydrogenation and a method of preparing 1,3-butadiene using the reactor.

The above and other objects can be accomplished by the present invention described below.

Technical Solution

In accordance with one aspect of the present invention, provided is a catalyst system for oxidative dehydrogenation, wherein a reactor is filled with a catalyst for oxidative dehydrogenation in an n-layer structure (n being an integer of 2 or more), wherein the catalyst is diluted and the reactor is filled with the diluted catalyst so that each layer of the n-layer structure satisfies Equations 1 and 2 below.

$$X \text{ wt \%} + Y \text{ wt \%} + Z \text{ wt \%} = 100 \text{ wt \%}, \quad \text{[Equation 1]}$$

wherein X represents a content of $AB_2O_4$ and is 3 to 30, wherein A is one or more selected from the group consisting of copper (Cu), radium (Ra), barium (Ba), strontium (Sr), calcium (Ca), beryllium (Be), zinc (Zn), magnesium (Mg), manganese (Mn), cerium (Ce), zirconium (Zr), lanthanum (La), and cobalt (Co) and B is iron (Fe); Y is a content of a porous support and is 20 to 97; and Z is a content of one or more dilution fillers selected from alumina, silica, silicon carbide, zirconia, titania, and cordierite and is 0 to 77.

$$X_n > X_{n-1}, \quad \text{[Equation 2]}$$

wherein, with respect to the direction in which reactants are fed into the reactor, $X_n$ represents X for the n-th layer, and $X_{n-1}$ represents X for the (n−1)th layer.

In accordance with another aspect of the present invention, provided is a catalyst system for oxidative dehydrogenation, wherein a reactor is filled with a catalyst for oxidative dehydrogenation, wherein the catalyst is diluted and the reactor is filled with the diluted catalyst so as to satisfy Equation 6 below.

$$X \text{ wt \%} + Y \text{ wt \%} + Z \text{ wt \%} = 100 \text{ wt \%}, \quad \text{[Equation 6]}$$

wherein X is a content of $AB_2O_4$ and is 5 to 25, wherein A is one or more selected from the group consisting of copper (Cu), radium (Ra), barium (Ba), strontium (Sr), calcium (Ca), beryllium (Be), zinc (Zn), magnesium (Mg), manganese (Mn), cerium (Ce), zirconium (Zr), lanthanum (La), and cobalt (Co) and B is iron (Fe); Y is a content of a porous support and is 25 to 85; and Z is a content of one or more selected from alumina, silica, silicon carbide, zirconia, titania, and cordierite and is 10 to 70.

In accordance with another aspect of the present invention, provided is a reactor for preparing butadiene including the catalyst system for oxidative dehydrogenation.

In accordance with yet another aspect of the present invention, provided is a method of preparing 1,3-butadiene including performing oxidative dehydrogenation using the reactor for preparing butadiene of the present invention, wherein the oxidative dehydrogenation is performed while continuously passing reactants containing a C4 compound including normal butene through the catalyst bed of the reactor.

Advantageous Effects

As apparent from the foregoing, the present invention advantageously provides a catalyst system for oxidative dehydrogenation, wherein a catalyst having a porous support on which an active ingredient is uniformly and firmly coated is diluted in a dilution filler and a reactor is filled with the diluted catalyst, or a reactor is filled with a catalyst for oxidative dehydrogenation so that the concentration of an active ingredient included in the catalyst gradually increases in the direction from reactants inlet in which reactants are fed into the reactor to products outlet. When the catalyst system according to the present invention is used, it is possible to effectively control distribution of heat generated inside a reactor during oxidative dehydrogenation without adding a separate apparatus or changing the conventional manufacturing facilities, and thus to improve conversion rate, selectivity, and yield. In addition, catalyst deterioration can be reduced, thereby improving long-term stability of a catalyst.

DESCRIPTION OF DRAWINGS

FIG. 1 is a graph showing temperature distribution inside a catalyst bed when oxidative dehydrogenation is performed using the catalyst system according to Example 1.

FIG. 2 is a graph showing temperature distribution inside a catalyst bed when oxidative dehydrogenation is performed using the catalyst system according to Additional Comparative Example 3.

BEST MODE

Hereinafter, the catalyst system for oxidative dehydrogenation according to the present invention will be described in detail.

In the catalyst system for oxidative dehydrogenation according to the present invention, a catalyst for oxidative dehydrogenation is diluted to satisfy Equation 1 below, and a reactor is filled with the diluted catalyst.

$$X \text{ wt \%} + Y \text{ wt \%} + Z \text{ wt \%} = 100 \text{ wt \%},  \quad \text{[Equation 1]}$$

wherein X represents a content of $AB_2O_4$ and is 3 to 30, wherein A is one or more selected from the group consisting of copper (Cu), radium (Ra), barium (Ba), strontium (Sr), calcium (Ca), beryllium (Be), zinc (Zn), magnesium (Mg), manganese (Mn), cerium (Ce), zirconium (Zr), lanthanum (La), and cobalt (Co) and B is iron (Fe); Y is a content of a porous support and is 20 to 97; and Z is a content of one or more dilution fillers selected from alumina, silica, silicon carbide, zirconia, titania, and cordierite and is 0 to 77.

$$X_n > X_{n-1}, \quad \text{[Equation 2]}$$

wherein, with respect to the direction in which reactants are fed into the reactor, $X_n$ represents X for the n-th layer, and $X_{n-1}$ represents X for the (n−1)th layer.

According to the present invention, $AB_2O_4$ is the active ingredient of a catalyst, and the catalyst for oxidative dehydrogenation is a coating catalyst having a porous support coated with the active ingredient $AB_2O_4$.

For example, $AB_2O_4$ can be a zinc ferrite ($ZnFe_2O_4$), wherein A is zinc (Zn) and B is iron (Fe). In this case, the catalyst can exhibit excellent activity in oxidative dehydrogenation of normal butene, and can have high selectivity for 1,3-butadiene.

For example, $AB_2O_4$ can have an average particle diameter of 0.1 to 250 μm, 10 to 200 μm, 15 to 150 μm, 15 to 100 μm, 15 to 60 μm, or 25 to 60 μm. Within this range, coating of the active ingredient on the porous support can be easily performed, and the catalyst can have excellent activity, thereby improving reaction efficiency.

According to the present invention, $AB_2O_4$ having an average particle diameter within the above range can be selected, for example, using a sieving method.

For example, in Equation 1, X is preferably 3 to 30, 3 to 27, 3.5 to 20, 3.5 to 18, or 3.5 to 14. Within this range, reaction efficiency can be excellent, thereby improving yield, selectivity, and conversion rate.

For example, the porous support can have an average particle diameter of 3 to 7 mm or 4 to 6 mm. Within this range, reaction efficiency can be excellent, thereby improving conversion rate and selectivity.

For example, the porous support can have an average pore size of 50 to 200 μm or 100 to 150 μm. Within this range, coating of $AB_2O_4$ powder can be easy performed and desorption of the powder can be prevented.

According to the present invention, the average particle diameter and average pore size of the porous support can be measured, for example, using a method of calculating a surface area and an average pore size through adsorption isotherm of nitrogen by the BET method and the BJH (Barret-Joyner-Halenda) method, respectively, or using a mercury impregnation method.

The porous support can have a packing density of 0.8 to 1.5 kg/m³ or 0.9 to 1.3 kg/m³. Coating rate is determined based on the packing density. When the porous support has a packing density within this range, separation or desorption of the $AB_2O_4$ powder can be prevented, and the support can be easily coated with the powder. Further, when oxidative dehydrogenation is performed, the conversion rate of butene or 1,3-butadiene yield can be increased, and excessive increase in the temperature inside a catalyst bed can be suppressed, thereby increasing thermal stability.

According to the present invention, packing density is calculated by dividing mass capable of filling a tubular measuring cylinder to 100 cc by a volume value of 100 cc thereof.

The porous support is preferably spherical, hollow, or in the form of pellets. In this case, reaction efficiency can be excellent, thereby improving yield, selectivity, and conversion rate.

In the present invention, spherical, pellet, and hollow shapes are not particularly limited as long as they are within the ordinary range of those skilled in the art of porous support technology, and these shapes are clearly distinguished.

For example, the porous support can be one or more selected from the group consisting of alumina, silica, titania, zirconia, silicon carbide, and cordierite, and is preferably alumina or silica. In this case, mechanical strength for filling a reactor is satisfied and side reaction can be reduced.

More preferably, the porous support is alumina. In this case, mechanical strength can be ensured, and butadiene yield and selectivity can be prevented from being lowered by side reaction during oxidative dehydrogenation.

For example, in Equation 1, Y can be 20 to 97, 21 to 90, 21 to 86, 30 to 86, or 40 to 86. Within this range, catalytic activity and heat generation control can be excellent.

The coating catalyst of the present invention can further include an organic/inorganic binder when necessary. In this case, the binder can be included in an amount of 30 parts by weight or less, 0.1 to 20 parts by weight, or 0.1 to 10 parts by weight based on 100 parts by weight of $AB_2O_4$. Within this range, the abrasion resistance of the catalyst can be improved without significantly lowering the efficiency of oxidative dehydrogenation.

For example, the binder can include aluminum-silicate, methylcellulose, hydroxypropyl methylcellulose, or both. When the binder is contained in an appropriate amount, the abrasion resistance of the catalyst can be improved without significantly lowering the efficiency of oxidative dehydrogenation.

As another example, the coating catalyst of the present invention can be a binder-free catalyst. In this case, since side reaction is not caused by the binder, the conversion rate of normal butene and selectivity for butadiene can be greatly increased. In addition, since introduction of some components is omitted, a process of preparing the catalyst can be simplified, thereby reducing process costs.

According to the present invention, binder-free means that an organic or inorganic binder is omitted when preparing a catalyst and/or that a catalyst is prepared without the binder.

For example, a fixed-bed reactor can be filled with the catalyst for oxidative dehydrogenation according to the present invention in a 2- to 8-layer, 3- to 8-layer, 3- to 6-layer, or 3- to 5-layer structure. Within this range, distribution of heat generated inside the reactor can be effectively controlled without significantly increasing process costs. Thus, when butadiene is prepared, conversion rate, selectivity, and yield can be greatly improved, and long-term stability of the catalyst can be improved.

For example, the catalyst system of the present invention satisfies Equation 3 below. In this case, excessive heat generation in the catalyst bed can be effectively prevented during reaction. As a result, when butadiene is prepared, conversion rate, selectivity, yield, and long-term stability of the catalyst can be improved.

$$(X_n - X_{n-1}) \geq 2, \quad \text{[Equation 3]}$$

wherein $X_n$ represents X for the n-th layer, and $X_{n-1}$ represents X for the (n−1)th layer.

According to the present invention, at least one of the n layers can have a Z value greater than 0. When the coating catalyst is mixed with a dilution filler and a reactor is filled with the coating catalyst so that the concentration of the catalyst is gradually decreased, heat generation control can be effectively performed during reaction, thereby improving reaction efficiency.

According to the present invention, the dilution filler can be, for example, one or more selected from alumina, silica, silicon carbide, zirconia, titania, and cordierite, and is preferably one or more selected from alumina and silica. In this case, it is possible to suppress generation of excessive reaction heat while minimizing side reaction, thereby greatly improving the efficiency of oxidative dehydrogenation.

The catalyst system of the present invention satisfies Equation 4 below when at least one layer has a Z value other than 0. In this case, excessive temperature increase of the catalyst bed due to excessive heat may be suppressed, and thus productivity such as conversion rate, selectivity, and yield can be greatly improved when butadiene is prepared.

$$(Y_n - Y_{n-1}) \geq 15, \quad \text{[Equation 4]}$$

wherein $Y_n$ represents Y for the n-th layer, and $Y_{n-1}$ represents Y for the (n−1)th layer.

In addition, the catalyst system of the present invention satisfies Equation 5 below. In this case, heat generation due to oxidative dehydrogenation can be effectively controlled so that the activity or stability of the catalyst can be continuously maintained high and reaction efficiency can be improved.

$$(Z_{n-1} - Z_n) \geq 20, \quad \text{[Equation 5]}$$

wherein $Z_n$ represents Z for the n-th layer, and $Z_{n-1}$ represents Z for the (n−1)th layer.

As another example, in the catalyst system for oxidative dehydrogenation according to the present invention, a reactor is filled with the catalyst for oxidative dehydrogenation in an n-layer structure (n being an integer of 2 or more). In this case, the catalyst is diluted and the reactor is filled with the diluted catalyst so that each layer satisfies Equations 1 and 2. In addition, the porous support has a packing density of 0.8 to 1.5 $kg/m^3$ or 0.9 to 1.2 $kg/m^3$. In this case, separation or peeling of $AB_2O_4$ powder from the porous support can be prevented, and the support can be uniformly and firmly coated with the catalyst. In addition, heat generation inside the catalyst bed during oxidative dehydrogenation can be effectively controlled, and side reaction can be suppressed, thereby improving the conversion rate of butene, butadiene yield, and selectivity.

As a specific example, in the catalyst system for oxidative dehydrogenation according to the present invention, a reactor is filled with the catalyst for oxidative dehydrogenation in a three-layer structure. In this case, the catalyst is diluted and the reactor is filled with the diluted catalyst so that each layer satisfies Equations 1 and 2 below. With respect to the direction in which reactants are fed into the reactor, in the case of the first layer, X is 3.5 to 7; Y is 21.5 to 43; and Z is 50 to 75, in the case of the second layer, X is 7 to 10.5; Y is 43 to 64.5; and Z is 25 to 50, and in the case of the third layer, X is 13 to 18; Y is 82 to 87; and Z is 0 to 5. In this case, excessive temperature rise inside the catalyst bed can be effectively suppressed. Consequently, compared to the conventional catalyst system, the conversion rate of butene and selectivity for 1,3-butadiene can be improved.

$$X \text{ wt \%} + Y \text{ wt \%} + Z \text{ wt \%} = 100 \text{ wt \%}, \quad \text{[Equation 1]}$$

wherein X is a content of zinc ferrite powder wherein A is Zn and B is Fe, Y is a content of a porous support, and Z is a content of one or more dilution fillers selected from alumina, silica, silicon carbide, and zirconia, wherein the porous support is alumina having a packing density of 0.8 to 1.5 $kg/m^3$.

$$X_n > X_{n-1}, \quad \text{[Equation 2]}$$

wherein, with respect to the direction in which reactants are fed into the reactor, $X_n$ represents X for the n-th layer, and $X_{n-1}$ represents X for the (n−1)th layer, wherein n is the total number of layers and is 3.

As a preferred example, in the first layer, X is 3 to 4.5; Y is 20 to 35; and Z is 60.5 to 77, in the second layer, X is 5 to 8; Y is 40 to 50; and Z is 45 to 55, and in the third layer, X is 10 to 16; Y is 60 to 90; and Z is 0 to 30. In this case, excessive temperature rise inside the catalyst bed can be effectively suppressed. When oxidative dehydrogenation is performed using the catalyst system, side reaction can be suppressed, and the conversion rate of butene, selectivity for butadiene, and yield can be improved.

In addition, as another example, in the catalyst system of the present invention, the catalyst for oxidative dehydrogenation is diluted and a reactor is filled with the catalyst so as to satisfy Equation 6 below.

$$X \text{ wt \%} + Y \text{ wt \%} + Z \text{ wt \%} = 100 \text{ wt \%}, \quad \text{[Equation 6]}$$

wherein X is a content of $AB_2O_4$ and is 5 to 25, wherein A is one or more selected from the group consisting of copper (Cu), radium (Ra), barium (Ba), strontium (Sr), calcium (Ca), beryllium (Be), zinc (Zn), magnesium (Mg), manganese (Mn), cerium (Ce), zirconium (Zr), lanthanum (La), and cobalt (Co) and B is iron (Fe); Y is a content of a porous support and is 25 to 85; and Z is a content of one or more dilution fillers selected from alumina, silica, silicon carbide, zirconia, titania, and cordierite and is 10 to 70.

Hereinafter, a catalyst system for oxidative dehydrogenation according to another embodiment of the present invention, wherein the catalyst is diluted and a reactor for oxidative dehydrogenation is filled with the diluted catalyst so as to satisfy Equation 6, will be described. In explaining the system, the overlapping description with the incremental dilution filling system of the above-mentioned catalyst for oxidative dehydrogenation will be omitted.

In Equation 6, X is preferably 5 to 25, 7 to 20, 7 to 18, 7 to 14, 7 to 13.5, or 7 to 11. Within this range, reaction efficiency can be excellent, thereby improving yield, selectivity, and conversion rate.

In Equation 6, Y can be, for example, 25 to 85, 35 to 80, 36 to 75, 36.5 to 70, 36.5 to 60, or 40 to 50. Within this range, catalytic activity and catalyst stability can be maintained high, and the productivity of butadiene can be increased.

In Equation 6, Z can be, for example, 10 to 70, 20 to 70, or 40 to 60. Within this range, excessive heat generation due to oxidative dehydrogenation can be effectively suppressed, thereby improving catalyst stability and reaction efficiency.

As a preferred example, the porous support can have a packing density of 0.8 to 1.5 kg/m$^3$ or 0.9 to 1.2 kg/m$^3$. Within this range, the mechanical strength of the coating catalyst can be excellent, and separation or peeling of $AB_2O_4$ powder from the porous support can be prevented. In addition, heat generation in the catalyst bed during oxidative dehydrogenation can be effectively suppressed, and butadiene yield and selectivity for butadiene can be improved.

The catalyst system can be an oxidative-dehydrogenation catalyst system for preparation of 1,3-butadiene.

In addition, the present invention provides a reactor for preparing butadiene including the catalyst system and a method of preparing 1,3-butadiene using the reactor.

For example, the method of preparing 1,3-butadiene according to the present invention includes i) filling a reactor with the catalyst for oxidative dehydrogenation as a fixed bed; and ii) performing oxidative dehydrogenation while continuously passing reactants containing a C4 compound including normal butene through the catalyst bed of the reactor filled with the catalyst, wherein the reactor in step i) is a fixed-bed reactor filled with the catalyst for oxidative dehydrogenation in an n-layer structure (n being an integer of 2 or more) in a progressive dilution manner, wherein each stage of the n-stage structure satisfies Equations 1 and 2.

As another example, the method of preparing 1,3-butadiene according to the present invention includes i) filling a reactor with the catalyst for oxidative dehydrogenation as a fixed bed; and ii) performing oxidative dehydrogenation while continuously passing reactants containing a C4 compound including normal butene through the catalyst bed of the reactor filled with the catalyst, wherein the reactor in step i) is a fixed-bed reactor, wherein the catalyst for oxidative dehydrogenation is diluted and the fixed-bed reactor is filled with the diluted catalyst so as to satisfy Equation 6.

When a specific catalyst is diluted and a reactor is filled with the diluted catalyst, or a reactor is filled with a specific catalyst in a progressive dilution manner, and then oxidative dehydrogenation is performed, heat generation inside the reactor can be effectively controlled. In particular, when a fixed-bed reactor is filled with a specific catalyst for oxidative dehydrogenation in a progressive dilution manner, heat generation control effect can be maximized, allowing catalytic activity and catalyst stability to remain high over a long period of time. In addition, the conversion rate of butene, selectivity for butadiene, and yield can be greatly improved.

The C4 compound can include, for example, one or more normal butene selected from 2-butene (trans-2-butene, cis-2-butene) and 1-butene, and can optionally further include normal butane or C4 raffinate-3.

For example, the reactants can further include one or more selected from air, nitrogen, steam, and carbon dioxide, and preferably further includes nitrogen and steam.

As a specific example, the reactants can include a C4 compound, oxygen, steam, and nitrogen in a molar ratio of 1:0.1 to 1.5:1 to 15:0.5 to 10 or 1:0.5 to 1.2:5 to 12:0.5 to 5. In addition, the method of preparing butadiene according to the present invention shows excellent reaction efficiency and little generation of wastewater even when steam is used in a small amount (e.g., 1 to 10 mol or 5 to 10 mol based on 1 mol of the C4 compound). Ultimately, the method provides the effect of reducing wastewater treatment cost and the effect of reducing energy consumed in the process.

For example, the oxidative dehydrogenation reaction can be performed at a reaction temperature of 250 to 500° C., 300 to 450° C., 320 to 400° C., 330 to 380° C., or 350 to 370° C. Within this range, reaction efficiency can be excellent without greatly increasing energy cost, thereby increasing the productivity of 1,3-butadiene.

In addition, in oxidative dehydrogenation, the ΔT value calculated by Equation 7 below can be 105° C. or less, 104° C. or less, 90° C. or less, 80° C. or less, 70° C. or less, 60° C. or less, 50° C. or less, 40° C. or less, 20 to 70° C., or 20 to 45° C.

$$\Delta T(° C.) = \text{reaction temperature} - \text{the maximum temperature inside a catalyst bed} \quad \text{[Equation 7]}$$

According to the present invention, the maximum temperature inside the catalyst bed means the part of the catalyst bed with the highest temperature during reaction.

In addition, the maximum temperature inside the catalyst bed can be measured, for example, by connecting a thermocouple (TC) to a transfer device and then performing scanning while moving the thermocouple from the top of the reactor to the bottom of the reactor at constant velocity.

For example, oxidative dehydrogenation can be performed at a gas hourly space velocity (GHSV) of 50 to 2,000 $h^{-1}$, 50 to 1,500 $h^{-1}$, or 50 to 1,000 $h^{-1}$ based on normal butene. Within this range, reaction efficiency can be excellent, thereby improving conversion rate, selectivity, and yield.

In the present invention, the reactor is not particularly limited as long as the reactor includes the catalyst system for oxidative dehydrogenation, but can be, for example, a multi-tube reactor or a plate reactor.

Hereinafter, the present invention will be described in more detail with reference to the following preferred examples. However, these examples are provided for illustrative purposes only and should not be construed as limiting the scope and spirit of the present invention. In addition, it will be apparent to those skilled in the art that various changes and modifications can be made without departing from the spirit and scope of the present invention, and such changes and modifications are also within the scope of the appended claims.

PREPARATION EXAMPLE

1. Preparation of $ZnFe_2O_4$ Powder

2 L of aqueous ammonia adjusted to have a pH of 8 was prepared. In a separate container, a metal precursor solution containing 2 L of distilled water, 288.456 g of zinc chloride ($ZnCl_2$), and 1132.219 g of iron chloride ($FeCl_3$) was prepared. The prepared metal precursor solution was added dropwise to the prepared aqueous ammonia, and at the same time, 9 wt % aqueous ammonia was added thereto to adjust the pH to 8. To obtain a sample having a uniform composition, all of the metal precursor solution was added dropwise with stirring for 1 hour using an agitator, aged for 1 hour, and then the solution including precipitate was washed with 4 L of distilled water and the precipitate was separated by filtration. The separated precipitate was dried for 16 hours, and then burned at 650° C. to obtain $ZnFe_2O_4$ powder. The obtained powder was pulverized, and then powder having a size of 45 μm or less was selected using a sieving method.

2. Preparation of Coating Catalyst $ZnFe_2O_4$ powder quantified so that $ZnFe_2O_4$ has a ratio of 14 wt % or 27 wt % based on 100 wt % in total of $ZnFe_2O_4$ and alumina balls was dispersed in distilled water to prepare a catalyst slurry having a concentration of 10 to 30 wt %. Alumina balls having a packing density of 0.9 to 1.2 kg/m³ were added to a rotary chamber under a vacuum atmosphere. Then, the catalyst slurry was coated on the alumina balls having an average particle diameter of 5 mm by spraying the catalyst slurry while rotating the rotary chamber at about 30 to 50 rpm. When coating was performed, the rotary chamber was set to a temperature of 50 to 80° C. After the coating process was completed, a coating catalyst was prepared by drying the catalyst slurry-coated alumina balls in an oven set to 90 to 120° C. so that distilled water was evaporated.

EXAMPLES

Example 1

The coating catalyst having $ZnFe_2O_4$ in an amount of 14 wt % was mixed with alumina as a dilution filler as shown in Table 1, and a tubular reactor was filled with the catalyst in a three-layer structure and in a gradual dilution manner.

Then, the conversion rate of butene, selectivity for 1,3-butadiene, 1,3-butadiene yield, and selectivity for $CO_x$ were measured.

The C4 compound containing trans-2-butene and cis-2-butene, oxygen, steam, and nitrogen as reactants were mixed in a molar ratio of 1:1:8:1. At this time, the amount of each of the C4 compound, oxygen, and nitrogen was controlled using a mass flow controller, and the injection rate of steam was controlled using a liquid pump. The feed rate of reactants was set so that a gas hourly space velocity (GHSV) was 66 $h^{-1}$ based on normal butene in the C4 compound. The reaction was performed at the reaction temperature shown in Table 1 below.

TABLE 1

| | GHSV/mole ratio of butene:oxygen:steam:nitrogen = 66 $h^{-1}$/1:1:8:1, 355° C. | | |
|---|---|---|---|
| Classification | X [content of $ZnFe_2O_4$, wt %] | Y [content of porous support, wt %] | Z [content of dilution filler, wt %] |
| Third layer | 14 | 86 | 0 |
| Second layer | 10.5 | 64.5 | 25 |
| First layer | 7 | 43 | 50 |

* In table 1, each of X, Y, and Z is based on 100 wt % of the total amount thereof.

Example 2

A reactor was filled with the catalyst composition in a gradual dilution manner in a three-layer structure as shown in Table 2 below. Then, reaction was performed under the same conditions and in the same manner as in Example 1, except that the reaction was performed at the temperature specified in Table 2 below.

TABLE 2

| | GHSV/mole ratio of butene:oxygen:steam:nitrogen = 66 $h^{-1}$/1:1:8:1, 360° C. | | |
|---|---|---|---|
| Classification | X [content of $ZnFe_2O_4$, wt %] | Y [content of porous support, wt %] | Z [content of dilution filler, wt %] |
| Third layer | 14 | 86 | 0 |
| Second layer | 7 | 43 | 50 |
| First layer | 3.5 | 21.5 | 75 |

* In Table 2, each of X, Y, and Z is based on 100 wt % of the total amount thereof.

Example 3

The coating catalyst containing $ZnFe_2O_4$ in an amount of 14 wt % was diluted by mixing with a dilution filler as shown in Table 3 and a tubular reactor was filled with the diluted catalyst. Then, reaction was performed under the same conditions and in the same manner as in Example 1, except that reaction temperature was set to 365° C.

Example 4

The coating catalyst containing $ZnFe_2O_4$ in an amount of 27 wt % was diluted by mixing with a dilution filler as shown in Table 3 and a tubular reactor was filled with the diluted catalyst. Then, reaction was performed under the same conditions and in the same manner as in Example 1, except that reaction temperature was set to 340° C.

TABLE 3

| Classification | Reaction temperature (°C.) | GHSV/mole ratio of butene:oxygen:steam:nitrogen = 66 h$^{-1}$/1:1:8:1 | | |
|---|---|---|---|---|
| | | X [content of ZnFe$_2$O$_4$, wt %] | Y [content of porous support, wt %] | Z [content of dilution filler, wt %] |
| Example 3 | 365 | 7 | 43 | 50 |
| Example 4 | 340 | 13.5 | 36.5 | 50 |

* In Table 3, each of X, Y, and Z is based on 100 wt % of the total amount thereof.

Comparative Example 1

ZnFe$_2$O$_4$ powder prepared in the same manner as in Preparation Examples was kneaded with distilled water and an alcohol and then extrusion-molded to obtain pellets having a diameter of 2 mm and a length of 2 mm, followed by drying at 90° C. for 4 hours to obtain a catalyst in the form of pellets. 6 volume % of the prepared catalyst was mixed with 94 volume % of alumina balls, and the mixture was loaded into a reactor. Then, reaction was performed under the same conditions and in the same manner as in Example 1, except that reaction temperature was set to 365° C.

Comparative Example 2

ZnFe$_2$O$_4$ powder prepared in the same manner as in Preparation Examples was kneaded with distilled water and an alcohol and then extrusion-molded to obtain pellets having a diameter of 2 mm and a length of 2 mm, followed by drying at 90° C. for 4 hours to obtain a catalyst in the form of pellets. A reactor was filled with the prepared catalyst in a gradual dilution manner as shown in Table 4. Then, reaction was performed under the same conditions and in the same manner as in Example 1, except that reaction temperature was set to 375° C.

TABLE 4

| Classification | GHSV/mole ratio of butene:oxygen:steam:nitrogen = 66h$^{-1}$/1:1:8:1, 365° C. | | |
|---|---|---|---|
| | X [content of ZnFe$_2$O$_4$, wt %] | Y [content of porous support, wt %] | Z [content of dilution filler, wt %] |
| Third layer | 9 | — | 91 |
| Second layer | 6 | — | 94 |
| First layer | 3 | — | 97 |

* In Table 4, each of X and Z is based on 100 wt % of the total amount thereof.

Comparative Example 3

A tubular reactor was filled with the coating catalyst containing ZnFe$_2$O$_4$ in an amount of 14 wt %. In this case, addition of a dilution filler was omitted. Then, reaction was performed under the same conditions and in the same manner as in Example 3, except that reaction temperature was set to 343° C.

Comparative Example 4

A tubular reactor was filled with the coating catalyst containing ZnFe$_2$O$_4$ in an amount of 27 wt %. In this case, addition of a dilution filler was omitted. Then, reaction was performed under the same conditions and in the same manner as in Example 4, except that reaction temperature was set to 325° C.

TEST EXAMPLE

The products according to Examples and Comparative Examples were analyzed using gas chromatography. The conversion rate of butene, selectivity for 1,3-butadiene, 1,3-butadiene yield, selectivity for COx were calculated according to Equations 8, 9, and 10 below, respectively. The results are shown in Tables 5 and 6.

In addition, when oxidative dehydrogenation was performed using the catalyst systems according to Examples and Comparative Examples, the maximum temperature inside a catalyst bed was analyzed while moving a thermocouple in a thermo-well at the center of a reactor from the inlet of the reactor to the outlet of the reactor at a constant velocity of 4 mm per second.

Conversion rate (%) = [(Number of moles of butene reacted)/(Number of moles of butene supplied)]×100  [Equation 8]

Selectivity (%) = [(Number of moles of 1,3-butadiene or CO$_x$ generated)/(Number of moles of butene reacted)]×100  [Equation 9]

Yield (%) = [(Number of moles of 1,3-butadiene generated)/(Number of moles of butene supplied)]×100  [Equation 10]

TABLE 5

| | Conversion rate of butene (%) | Selectivity for 1,3-butadiene (%) | Yield of 1,3-butadiene yield (%) | Selectivity for CO$_x$ (%) | Hot spot (° C.) | ΔT (° C.) |
|---|---|---|---|---|---|---|
| Example 1 | 89.8 | 88.8 | 79.7 | 9.8 | 400 | 65 |
| Example 2 | 91.2 | 91.7 | 83.6 | 7.1 | 397 | 37 |
| Comparative Example 1 | 79.6 | 89.3 | 71.1 | 9.1 | 400 | 35 |
| Comparative Example 2 | 83.9 | 88.4 | 74.2 | 10.2 | 415 | 40 |

ΔT (° C.): Difference between the maximum temperature inside a catalyst bed and the reaction temperature set during reaction As shown in Table 5, compared with Comparative Examples 1 and 2, in the case of Examples 1 and 2 using the catalyst system according to the present invention, although oxidative dehydrogenation was performed at a relatively low reaction temperature, it was confirmed that the conversion rate of butene, selectivity for 1,3-butadiene, and 1,3-butadiene yield were excellent. In particular, when the catalyst system according to Example 2 was used, the efficiency and activity of oxidative dehydrogenation were excellent. In addition, considering that the difference between the maximum temperature inside a catalyst bed and the reaction temperature was small, it was confirmed that heat generated inside a reactor was effectively controlled.

On the other hand, in the case of the catalyst system according to Comparative Example 1, wherein the catalyst in the form of pellets prepared using $ZnFe_2O_4$ powder was diluted by mixing a dilution filler and a reactor was filled with the diluted catalyst, although reaction was performed at a relatively high reaction temperature, it was confirmed that reaction activity was significantly lower than in the cases of Examples. In addition, in the case of Comparative Example 2, although the catalyst in the form of pellets prepared using $ZnFe_2O_4$ powder was diluted by mixing with a dilution filler and a reactor was filled with the diluted catalyst in a gradual dilution manner, it was confirmed that reaction activity was lower than in Examples.

From the above results, it can be seen that, when the catalyst system, in which a catalyst having a porous support on which $ZnFe_2O_4$ is coated in a predetermined ratio is diluted with a dilution filler and a reactor is filled with the diluted catalyst in a gradual dilution manner, is used to perform oxidative dehydrogenation, the activity of oxidative dehydrogenation is greatly improved. In addition, it can be judged that this is because heat generation inside the reactor is controlled by the novel catalyst system according to the present invention, thereby providing a reaction system with a stable temperature gradient. In addition, from the results of Examples 1 and 2, it can be seen that, when the reactor is filled with the coating catalyst in a gradual dilution manner, dilution ratio affects reaction activity.

On the other hand, compared with Example 3, in the case of Comparative Example 3 in which the same concentration of the coating catalyst was used as in Example 3, even though reaction temperature was set to be as low as 22° C., it was confirmed that the maximum temperature inside a catalyst bed was higher by 10° C., and reaction activity was significantly decreased. In the case of Comparative Example 4, although the maximum temperature inside a catalyst bed was the highest, it was confirmed that reaction activity was significantly decreased.

ADDITIONAL EXAMPLES AND COMPARATIVE EXAMPLES

Additional Example 1

Reaction was performed under the same conditions and in the same manner as in Example 1, except that silicon carbide was used as a dilution filler.

Additional Example 2

Reaction was performed under the same conditions and in the same manner as in Example 1, except that zirconia was used as a dilution filler.

Additional Comparative Example 1

Reaction was performed under the same conditions and in the same manner as in Example 1, except that, when a coating catalyst was prepared, alumina balls having a packing density of 0.5 kg/m³ were used.

Additional Comparative Example 2

Reaction was performed under the same conditions and in the same manner as in Example 1, except that, when a

TABLE 6

| | Conversion rate of butene (%) | Selectivity for 1,3-butadiene (%) | Yield of 1,3-butadiene (%) | Selectivity for $CO_x$ (%) | Hot spot (° C.) | ΔT (° C.) |
|---|---|---|---|---|---|---|
| Example 3 | 90.4 | 89.0 | 80.5 | 9.8 | 453 | 88 |
| Comparative Example 3 | 88.3 | 88.5 | 78.1 | 10.1 | 443 | 100 |
| Example 4 | 86.1 | 85.8 | 73.9 | 11.3 | 444 | 104 |
| Comparative Example 4 | 82.7 | 86.6 | 71.6 | 12.0 | 471 | 146 |

ΔT (° C.): Difference between the maximum temperature inside a catalyst bed and the reaction temperature set during reaction As shown in Table 6, in the case of the catalyst systems (Examples 3 and 4) in which the coating catalyst is homogeneously diluted with a dilution filler, compared with the systems of Comparative Examples 3 and 4 in which the same coating catalyst was used, but the coating catalyst was not diluted, it was confirmed that the conversion rate of butene, selectivity for 1,3-butadiene, and 1,3-butadiene yield were excellent, and selectivity for COx as a side reaction product and the maximum temperature inside a catalyst bed were significantly decreased. In addition, it was confirmed that this improvement effect was even better when a coating catalyst having a coating ratio of 14 wt % was used.

coating catalyst was prepared, alumina balls having a packing density of 2.0 kg/m³ were used.

Additional Comparative Example 3

$ZnFe_2O_4$ powder prepared in the same manner as in Preparation Examples was kneaded with distilled water and an alcohol and then extrusion-molded to obtain pellets having a diameter of 5 mm and a length of 5 mm, followed by drying at 90° C. for 4 hours to obtain a catalyst in the form of pellets. A reactor was filled with the prepared catalyst. In this case, addition of a dilution filler was omitted. Then, reaction was performed under the same conditions and in the same manner as in Example 1, except that reaction temperature was set to 291° C.

The products prepared according to the Additional Examples and Additional Comparative Examples were analyzed in the same manner as described above, and the results are shown in Table 7.

TABLE 7

|  | Conversion rate of butene (%) | Selectivity for 1,3-butadiene (%) | Yield of 1,3-butadiene (%) | Selectivity for $CO_x$ (%) | Maximum temperature inside catalyst bed (° C.) | ΔT (° C.) |
|---|---|---|---|---|---|---|
| Additional Example 1 | 89.2 | 87.4 | 78.0 | 10.5 | 401 | 46 |
| Additional Example 2 | 86.7 | 87.5 | 75.9 | 11.1 | 407 | 52 |
| Additional Comparative Example 1 | 57.2 | 91.5 | 52.3 | 6.9 | 407 | 52 |
| Additional Comparative Example 2 | 80.1 | 87.0 | 69.7 | 11.0 | 419 | 64 |
| Additional Comparative Example 3 | 79.4 | 83.9 | 66.6 | 13.7 | 474 | 183 |

ΔT (° C.): Difference between the maximum temperature inside a catalyst bed and the reaction temperature set during reaction As shown in Table 7, in the case of Additional Examples 1 and 2 in which silicon carbide and zirconia were used as the dilution filler, respectively, the maximum temperature inside a catalyst bed was equal to or lower than that of Additional Comparative Examples 1 and 2, and the conversion rate of butene, selectivity for 1,3-butadiene, and 1,3-butadiene yield were excellent.

In addition, when alumina having a packing density outside the range of the present invention was used as the porous support, it was confirmed that the effect of suppressing overheating of the catalyst bed was insufficient even though the catalyst was diluted and supplied to satisfy Equations 1 and 2, and that the conversion rate of butene and butadiene yield were significantly reduced. In particular, when the packing density was less than the lower limit of the present invention (Additional Comparative Example 1), it was confirmed that the conversion rate of butene and butadiene yield were significantly reduced.

In addition, when mixing of the porous support and the dilution filler was omitted, as shown in Table 7, it was confirmed that the temperature inside the catalyst bed was considerably high because heat generation was not effectively controlled, and selectivity for COx as a side reaction product was considerably increased. The lifespan of the catalyst is expected to be considerably short.

FIG. 1 is a graph showing the temperature distribution of the catalyst bed when oxidative dehydrogenation is performed using the catalyst system according to Example 1, and FIG. 2 is a graph showing the temperature distribution of the catalyst bed when oxidative dehydrogenation is performed using the catalyst system according to Additional Comparative Example 3 (conventional technology).

Referring to these results, when the catalyst system according to the present invention was used, heat generation was effectively controlled, and thus the temperature inside the catalyst bed was kept relatively stable. On the other hand, when the catalyst system of Additional Comparative Example 3 was used, it was confirmed that the temperature inside the catalyst bed was drastically increased at the beginning of reaction, and thereafter was drastically decreased.

According to the results of the experiments, when the catalyst system according to the present invention is used, heat generated inside a reactor can be effectively controlled. Thus, the present invention can provide a reaction system with a stable temperature gradient. In addition, even when the maximum temperature inside a catalyst bed is low, high reaction activity and stability can be provided. Therefore, the catalyst system of the present invention can improve the efficiency of oxidative dehydrogenation.

The invention claimed is:

1. A catalyst system for oxidative dehydrogenation, wherein a reactor is filled with a catalyst for oxidative dehydrogenation in an n-layer structure (n being an integer of 2 or more), wherein the catalyst is diluted and the reactor is filled with the diluted catalyst so that each layer of the n-layer structure satisfies Equations 1 and 2 below:

$X$ wt %+$Y$ wt %+$Z$ wt %=100 wt %, [Equation 1]

wherein X represents an amount of $AB_2O_4$ and is 3 to 30, wherein A is one or more selected from the group consisting of copper (Cu), radium (Ra), barium (Ba), strontium (Sr), calcium (Ca), beryllium (Be), zinc (Zn), magnesium (Mg), manganese (Mn), cerium (Ce), zirconium (Zr), lanthanum (La), and cobalt (Co) and B is iron (Fe);

Y is an amount of a porous support and is 20 to 97; and

Z is an amount of one or more dilution fillers selected from alumina, silica, silicon carbide, zirconia, titania, and cordierite and is 0 to 77;

$X_n > X_{n-1}$, [Equation 2]

wherein, with respect to a direction in which reactants are fed into the reactor, $X_n$ represents an amount of X for an n-th layer, and $X_{n-1}$ represents an amount of X for an (n−1)th layer; and wherein the catalyst system satisfies Equation 5 below:

$(Z_{n-1} - Z_n) \geq 20$, [Equation 5]

wherein $Z_n$ represents an amount of Z for the n-th layer, and $Z_{n-1}$ represents an amount of Z for the (n−1)th layer.

2. The catalyst system according to claim 1, wherein n is an integer of 2 to 8.

3. The catalyst system according to claim 1, wherein the catalyst system satisfies Equation 3 below:

$(X_n - X_{n-1}) \geq 2$, [Equation 3]

wherein $X_n$ represents an amount of X for an n-th layer, and $X_{n-1}$ represents an amount of X for an (n−1)th layer.

4. The catalyst system according to claim 1, wherein at least one of the n layers has a Z value greater than 0.

5. The catalyst system according to claim 1, wherein, when at least one layer has a Z value other than 0, the catalyst system satisfies Equation 4 below:

$$(Yn-Yn-1) \geq 15, \quad \text{[Equation 4]}$$

wherein $Y_n$ represents an amount of Y for the n-th layer, and $Y_{n-1}$ represents an amount of Y for the (n−1)th layer.

6. The catalyst system according to claim 1, wherein $AB_2O_4$ is a coating catalyst coated on the porous support.

7. The catalyst system according to claim 6, wherein the coating catalyst is a binder-free catalyst.

8. The catalyst system according to claim 1, wherein $AB_2O_4$ is a zinc ferrite, wherein A is Zn and B is Fe.

9. The catalyst system according to claim 1, wherein the porous support is one or more selected from the group consisting of alumina, silica, titania, zirconia, silicon carbide, and cordierite.

10. The catalyst system according to claim 1, wherein the porous support has an average pore size of 50 to 200 μm.

11. The catalyst system according to claim 1, wherein the porous support has a packing density of 0.8 to 1.5 kg/m³.

12. A catalyst system for oxidative dehydrogenation, wherein a reactor is filled with a catalyst for oxidative dehydrogenation,
wherein the catalyst is diluted and the reactor is filled with the diluted catalyst so as to satisfy Equation 6 below:

$$X \text{ wt }\% + Y \text{ wt }\% + Z \text{ wt }\% = 100 \text{ wt }\%, \quad \text{[Equation 6]}$$

wherein X is an amount of $AB_2O_4$ and is 5 to 25 wt % wherein A is one or more selected from the group consisting of copper (Cu), radium (Ra), barium (Ba), strontium (Sr), calcium (Ca), beryllium (Be), zinc (Zn), magnesium (Mg), manganese (Mn), cerium (Ce), zirconium (Zr), lanthanum (La), and cobalt (Co) and B is iron (Fe);

Y is an amount of a porous support and is 25 to 85 wt %; and

Z is an amount of one or more dilution fillers selected from alumina, silica, silicon carbide, zirconia, titania, and cordierite and is 10 to 70 wt %.

13. A catalyst system for oxidative dehydrogenation, wherein a reactor is filled with a catalyst for oxidative dehydrogenation in an n-layer structure (n being an integer of 2 or more),
wherein the catalyst is diluted and the reactor is filled with the diluted catalyst so that each layer of the n-layer structure satisfies Equations 1 and 2 below:

$$X \text{ wt }\% + Y \text{ wt }\% + Z \text{ wt }\% = 100 \text{ wt }\%, \quad \text{[Equation 1]}$$

wherein X represents an amount of $AB_2O_4$ and is 3 to 30 wt %, wherein A is one or more selected from the group consisting of copper (Cu), radium (Ra), barium (Ba), strontium (Sr), calcium (Ca), beryllium (Be), zinc (Zn), magnesium (Mg), manganese (Mn), cerium (Ce), zirconium (Zr), lanthanum (La), and cobalt (Co) and B is iron (Fe);

Y is an amount of a porous support having a packing density of 0.8 to 1.5 kg/m³ and is 20 to 97 wt %; and Z is an amount of one or more dilution fillers selected from alumina, silica, silicon carbide, zirconia, titania, and cordierite and is 0 to 77 wt %;

$$X_n > X_{n-1}, \quad \text{[Equation 2]}$$

wherein, with respect to a direction in which reactants are fed into the reactor, $X_n$ represents X for an n-th layer, and $X_{n-1}$ represents X for an (n−1)th layer; and wherein at least one of the n layers has a Z value greater than 0.

* * * * *